(12) United States Patent
Kauffmann et al.

(10) Patent No.: US 12,399,169 B2
(45) Date of Patent: Aug. 26, 2025

(54) TANGENT FLOW HEMOLYSIS DETECTION BLOOD TESTING DEVICE

(71) Applicant: Siemens Healthcare Diagnostics Inc., Tarrytown, NY (US)

(72) Inventors: Aaron Kauffmann, Elkhart, IN (US); David Ledden, Elkhart, IN (US); Jennifer Samproni, Braintree, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 897 days.

(21) Appl. No.: 17/597,619

(22) PCT Filed: Dec. 5, 2019

(86) PCT No.: PCT/US2019/064636
§ 371 (c)(1),
(2) Date: Jan. 14, 2022

(87) PCT Pub. No.: WO2021/015808
PCT Pub. Date: Jan. 28, 2021

(65) Prior Publication Data
US 2022/0252578 A1 Aug. 11, 2022

Related U.S. Application Data

(60) Provisional application No. 62/876,211, filed on Jul. 19, 2019.

(51) Int. Cl.
*G01N 33/52* (2006.01)
*B01L 3/00* (2006.01)
*G01N 1/34* (2006.01)

(52) U.S. Cl.
CPC .......... *G01N 33/526* (2013.01); *B01L 3/5023* (2013.01); *B01L 3/502753* (2013.01);
(Continued)

(58) Field of Classification Search
CPC ....... B01L 2300/042; B01L 2300/0681; B01L 2300/069; B01L 3/5023; B01L 3/502753;
(Continued)

(56) References Cited

U.S. PATENT DOCUMENTS

| 484,487 | A | 10/1892 | Wunderlich |
| 3,954,623 | A | 5/1976 | Hammer et al. |

(Continued)

FOREIGN PATENT DOCUMENTS

| CN | 2240724 Y | 11/1996 |
| EP | 0597268 A1 | 5/1994 |

(Continued)

OTHER PUBLICATIONS

International Search Report and Written Opinion of International Application No. PCT/US2019/064636 dated Feb. 11, 2020.
(Continued)

*Primary Examiner* — Jennifer Wecker

(57) ABSTRACT

A tangent flow hemolysis blood testing assembly, device and method are described herein. The presently disclosed and claimed inventive concept(s) relate to a device(s), kit(s), and method(s) for injecting a patient's liquid test sample into a reaction vessel. More specifically, the presently disclosed and claimed inventive concept(s) relate to an improved liquid test sample injection device that comprises a plug that forms an airtight seal that facilitates the active injection of a liquid test sample into a reaction vessel, and kits and methods of use related thereto.

19 Claims, 3 Drawing Sheets

(52) U.S. Cl.
CPC .......... *G01N 1/34* (2013.01); *B01L 2300/042* (2013.01); *B01L 2300/0681* (2013.01); *B01L 2300/069* (2013.01)

(58) Field of Classification Search
CPC ...... G01N 1/34; G01N 33/491; G01N 33/526; G01N 33/726
See application file for complete search history.

(56) References Cited

U.S. PATENT DOCUMENTS

| | | |
|---|---|---|
| 4,844,871 A | 7/1989 | Polaschegg |
| 5,125,415 A | 6/1992 | Bell |
| 5,330,420 A | 7/1994 | Lee |
| 5,876,605 A | 3/1999 | Kitajima et al. |
| 5,979,669 A | 11/1999 | Kitajima et al. |
| 5,996,811 A | 12/1999 | Kitajima et al. |
| 6,045,699 A | 4/2000 | Yazawa et al. |
| 6,196,998 B1 | 3/2001 | Jansen et al. |
| 6,217,540 B1 | 4/2001 | Kitajima et al. |
| 6,220,453 B1 | 4/2001 | Kitajima et al. |
| 6,225,130 B1 | 5/2001 | Kitajima et al. |
| 6,280,621 B1 | 8/2001 | Yazawa et al. |
| 6,328,167 B1 | 12/2001 | Seshimoto et al. |
| 6,375,856 B1 | 4/2002 | Seshimoto et al. |
| 6,383,818 B1 | 5/2002 | Arai et al. |
| 6,387,290 B1 | 5/2002 | Brody et al. |
| 6,405,876 B1 | 6/2002 | Seshimoto et al. |
| 6,659,288 B2 | 12/2003 | Amano et al. |
| 6,659,975 B2 | 12/2003 | Amano et al. |
| 6,936,473 B2 | 8/2005 | Nanba et al. |
| RE39,457 E | 1/2007 | Guirguis |
| 7,323,144 B2 | 1/2008 | Arai et al. |
| 7,407,578 B2 | 8/2008 | Sakaino et al. |
| 7,500,569 B2 | 3/2009 | Manoussakis et al. |
| 7,896,818 B2 | 3/2011 | Fremming et al. |
| 7,927,810 B2 | 4/2011 | Togawa et al. |
| 8,057,672 B2 | 11/2011 | Chung et al. |
| 8,444,621 B2 | 5/2013 | Fremming et al. |
| 8,535,617 B2 | 9/2013 | MacDonald et al. |
| 8,574,497 B2 | 11/2013 | Pfaff |
| 8,846,333 B2 | 9/2014 | Karlsson |
| 8,865,003 B2 | 10/2014 | Yang |
| 8,999,268 B2 | 4/2015 | Egger-Cimenti et al. |
| 9,028,688 B2 | 5/2015 | Okamoto et al. |
| 9,261,494 B2 | 2/2016 | Choi et al. |
| 9,283,313 B2 | 3/2016 | Huemer |
| 9,322,761 B2 | 4/2016 | Miller |
| 9,427,707 B2 | 8/2016 | Montagu et al. |
| 9,517,026 B2 | 12/2016 | Gelfand et al. |
| 9,597,028 B2 | 3/2017 | Marchiarullo |
| 9,757,095 B2 | 9/2017 | Terbrueggen et al. |
| 9,816,979 B2 | 11/2017 | Kelso et al. |
| 9,983,199 B2 | 5/2018 | Karlsson |
| 9,993,816 B2 | 6/2018 | Biesbrouck |
| 10,111,610 B2 | 10/2018 | Tan et al. |
| 2001/0039057 A1 | 11/2001 | Douglas et al. |
| 2002/0036170 A1 | 3/2002 | Harvey et al. |
| 2003/0185707 A1 | 10/2003 | Iwaki et al. |
| 2004/0035792 A1 | 2/2004 | Rauch et al. |
| 2005/0227370 A1 | 10/2005 | Ramel et al. |
| 2006/0016747 A1 | 1/2006 | Sakaino et al. |
| 2008/0003141 A1 | 1/2008 | Iketani |
| 2008/0017577 A1 | 1/2008 | Yi et al. |
| 2010/0111763 A1* | 5/2010 | Kahn .................. G01N 33/726 422/400 |
| 2011/0076697 A1 | 3/2011 | Ruvinsky et al. |
| 2011/0144593 A1* | 6/2011 | Fremming ............. A61B 5/154 604/199 |
| 2012/0086938 A1 | 4/2012 | Folkenberg |
| 2012/0232803 A1 | 9/2012 | Viola et al. |
| 2013/0040333 A1 | 2/2013 | Karlsson |
| 2013/0184188 A1 | 7/2013 | Ewart et al. |
| 2014/0305196 A1 | 10/2014 | Ellis et al. |
| 2014/0329268 A1 | 11/2014 | Karlsson |
| 2015/0090674 A1 | 4/2015 | Lee et al. |
| 2015/0153323 A1 | 6/2015 | Huemer |
| 2016/0074569 A1 | 3/2016 | Schuetz et al. |
| 2016/0096148 A1 | 4/2016 | Schuetz et al. |
| 2016/0106353 A1 | 4/2016 | Schuetz et al. |
| 2016/0106907 A1 | 4/2016 | Winkler et al. |
| 2016/0202237 A1 | 7/2016 | Zeng et al. |
| 2016/0258937 A1 | 9/2016 | Ellington et al. |
| 2016/0258945 A1 | 9/2016 | Malima et al. |
| 2016/0313298 A1 | 10/2016 | Wright et al. |
| 2017/0059550 A1 | 3/2017 | Bokka Srinivasa Rao et al. |
| 2017/0095190 A1 | 4/2017 | Sloan et al. |
| 2017/0108516 A1 | 4/2017 | Ledden et al. |
| 2017/0241977 A1 | 8/2017 | Wilson et al. |
| 2017/0248618 A1 | 8/2017 | Baxter et al. |
| 2017/0252706 A1 | 9/2017 | Xu et al. |
| 2017/0299481 A1 | 10/2017 | Laugham, Jr. |
| 2017/0328896 A1 | 11/2017 | Luloh et al. |
| 2017/0354361 A1* | 12/2017 | Tan .................. A61B 5/150022 |
| 2017/0354362 A1 | 12/2017 | Xu et al. |
| 2018/0125464 A1 | 5/2018 | Kolb et al. |
| 2018/0128807 A1 | 5/2018 | Shizaka et al. |
| 2018/0128844 A1 | 5/2018 | Shizaka et al. |
| 2018/0136194 A1 | 5/2018 | Sinn Blandy et al. |
| 2018/0143116 A1 | 5/2018 | Urano et al. |
| 2018/0230508 A1* | 8/2018 | Idelevich ................ B01L 3/502 |
| 2018/0304261 A1 | 10/2018 | Ho et al. |
| 2018/0321228 A1 | 11/2018 | Cooper et al. |
| 2019/0046715 A1 | 2/2019 | Margraf et al. |
| 2019/0072539 A1* | 3/2019 | Eriksson ............. G01N 33/491 |

FOREIGN PATENT DOCUMENTS

| | | |
|---|---|---|
| JP | 2015503104 A | 1/2015 |
| JP | 2015530566 A | 10/2015 |
| WO | 2007000986 A1 | 1/2007 |
| WO | 2009110089 A1 | 9/2009 |
| WO | 2010113355 A1 | 10/2010 |
| WO | 2011033000 A2 | 3/2011 |
| WO | 2014019254 A1 | 2/2014 |
| WO | 2014172234 A1 | 10/2014 |
| WO | 2014207140 A1 | 12/2014 |
| WO | 2014207150 A1 | 12/2014 |
| WO | 2015191450 A1 | 12/2015 |
| WO | 2018065626 A1 | 4/2018 |
| WO | 2018226994 A1 | 12/2018 |
| WO | 2019025914 A1 | 2/2019 |
| WO | 2020118018 A1 | 6/2020 |
| WO | 2020118021 A1 | 6/2020 |
| WO | 2020185272 A1 | 9/2020 |

OTHER PUBLICATIONS

Liu et al., "Membrane-based, sedimentation-assisted plasma separator for point-of-care applications", Nov. 5, 2013, Anal Chem. 85(21), pp. 1-17.

Adiga et al., "Hemolytic index—A tool to measure hemolysis in vitro", 2016, IOSR Journal of Biotechnology and Biochemistry, vol. 2, Issue 2, pp. 49-52.

McCaughey et al., "Current Methods of Haemolysis Detection and Reporting as a Source of Risk to Patient Safety: a Narrative Review", 2016, Clin Biochem Rev 37 (4), pp. 143-151.

Peter J. Howanitz MD, Presentation on Hemolysis, <https://www.slideserve.com/altessa/peter-j-howanitz-md>, Jul. 20, 2014, pp. 1-30.

Zhou et al., "Optofluidic Sensor for Inline Hemolysis Detection on Whole Blood", Feb. 2018, ACS Sensors, 3, pp. 784-791.

* cited by examiner

TANGENT FLOW HEMOLYSIS DETECTION BLOOD TESTING DEVICE

The subject application claims benefit under 35 USC § 119(e) of U.S. provisional Application No. 62/876,211, filed Jul. 19, 2019. The entire contents of the above-referenced patent application are hereby expressly incorporated herein by reference.

STATEMENT REGARDING FEDERALLY SPONSORED RESEARCH AND DEVELOPMENT

Not Applicable.

BACKGROUND

Point-of-care testing refers generally to medical testing at or near the site of patient care, such as in an emergency room. A desired outcome of such tests is often rapid and accurate lab results to determine a next course of action in patient care. A number of such point of care tests involve analysis of a patient's liquid test sample, such as, by way of example only, a patient's blood sample.

Many of these tests use whole blood, plasma separated from larger bodies such as erythrocytes and leukocytes, or serum. In these samples there are often residual broken blood cells as a result of hemolysis due to, for instance, imperfections in obtaining the sample from the patient, pre-analytical blood sample handling, the whole blood separation process, and/or due to patient conditions, such as, by way of example, hemolytic anemia. In certain cases, these hemolysed cells can interfere with the integrity of analytical test results.

For example, free hemoglobin in the patient's blood sample (resulting from hemolysis) may cause interference in a number of tests, thereby leading to a signal reduction, reduced measurement accuracy, or false positive results. As an example, it has been found that the potassium concentration in a patient's hemolyzed blood sample may increase significantly and cause a high risk of misdiagnosis in a diagnostic test for potassium levels. Hemolysis can also interfere, for example, with readings of albumin, amylase, bilirubin, calcium, cholesterol, alkaline phosphate, alanine aminotransferase, cardiac troponin I, and cardiac troponin T.

To determine whether hemolysis has occurred, a number of tests have been developed. One common reagent used for determining hemoglobin levels or hemolysis in a blood sample is Drabkin's Reagent. Drabkin's Reagent comprises a mixture of sodium bicarbonate, potassium ferricyanide, and potassium cyanide which collectively function to lyse red blood cells in a patient's blood sample followed by the subsequent conversion of hemoglobin to cyanmethemoglobin, which is then measured on a spectrophotometer using a single wavelength. As such, Drabkin's Reagent may be used to measure intracellular hemoglobin as well as potentially free hemoglobin in a plasma or serum sample.

To process a sample with Drabkin's Regent, a spectrophotometer is set to a wavelength of about 540 nm and absorbance is blanked to a water reference. Following the blanking, test tubes are prepared for a water reference and samples. In one example, five (5) milliliters of Drabkin's Reagent solution are added to each test tube. Twenty (20) microliters of a patient's blood sample is then added to the sample test tubes as needed and pipetted up and down multiple times to lyse the blood sample. The sample is left for a set period of time (such as, by way of example, about fifteen (15) minutes) depending on ambient conditions to convert the hemoglobin into cyanmethemoglobin. The absorbance of the respective sample(s) is/are then read at a wavelength of about 540 nanometers. The results are then interpreted with a calibration curve.

However, as Drabkin's Reagent measures both intracellular and extracellular hemoglobin, it is not effective at providing an accurate picture of the extent of free hemoglobin present at a particular point in time in a patient's blood sample, such amount of free hemoglobin being indicative of hemolysis.

Some hemoglobin detection tests are described in published patent applications. For instance, international patent application WO2015191450 describes techniques for detecting hemolysis using a chromatographic detection pad. In addition, US patent application No. 20170248618 describes techniques for detecting hemolysis by using a membrane to separate blood from plasma and then determining a color of the plasma. Techniques are also described in the article "Membrane-Based, Sedimentation-Assisted Plasma Separator for Point of Care Applications", Changchun Liu et al. Analytical Chemistry 2013 85(21), 10463-10470. The techniques described in this article, however, require a large sample volume, long wait time, and secondary steps for hemolysis detection and quantification.

U.S. Pat. Nos. 7,896,818 and 8,444,621 both issued to Fremming et al disclose a sampler cap which may be used to transfer a test sample to an analyzer without removing the sample cap from a sampler. The sampler is a syringe; however, the sampler cap does not include any manner of determining whether hemolysis has occurred in the blood sample. As such, hemolyzed blood may be transferred into the analyzer which may cause interference in the performance of assays and tests.

Accordingly, there is a current need for an improved hemolysis detection and plasma separation device that is able to rapidly and accurately detect the amount of free hemoglobin present in a patient's blood sample as a result of hemolysis. It is to such devices, kits, and methods that the presently disclosed and/or claimed inventive concept(s) are directed.

BRIEF DESCRIPTION OF THE DRAWINGS

The accompanying drawings, which are incorporated in and constitute a part of this specification, illustrate one or more implementations described herein and, together with the description, explain these implementations. In the drawings.

DETAILED DESCRIPTION

Figure 1:
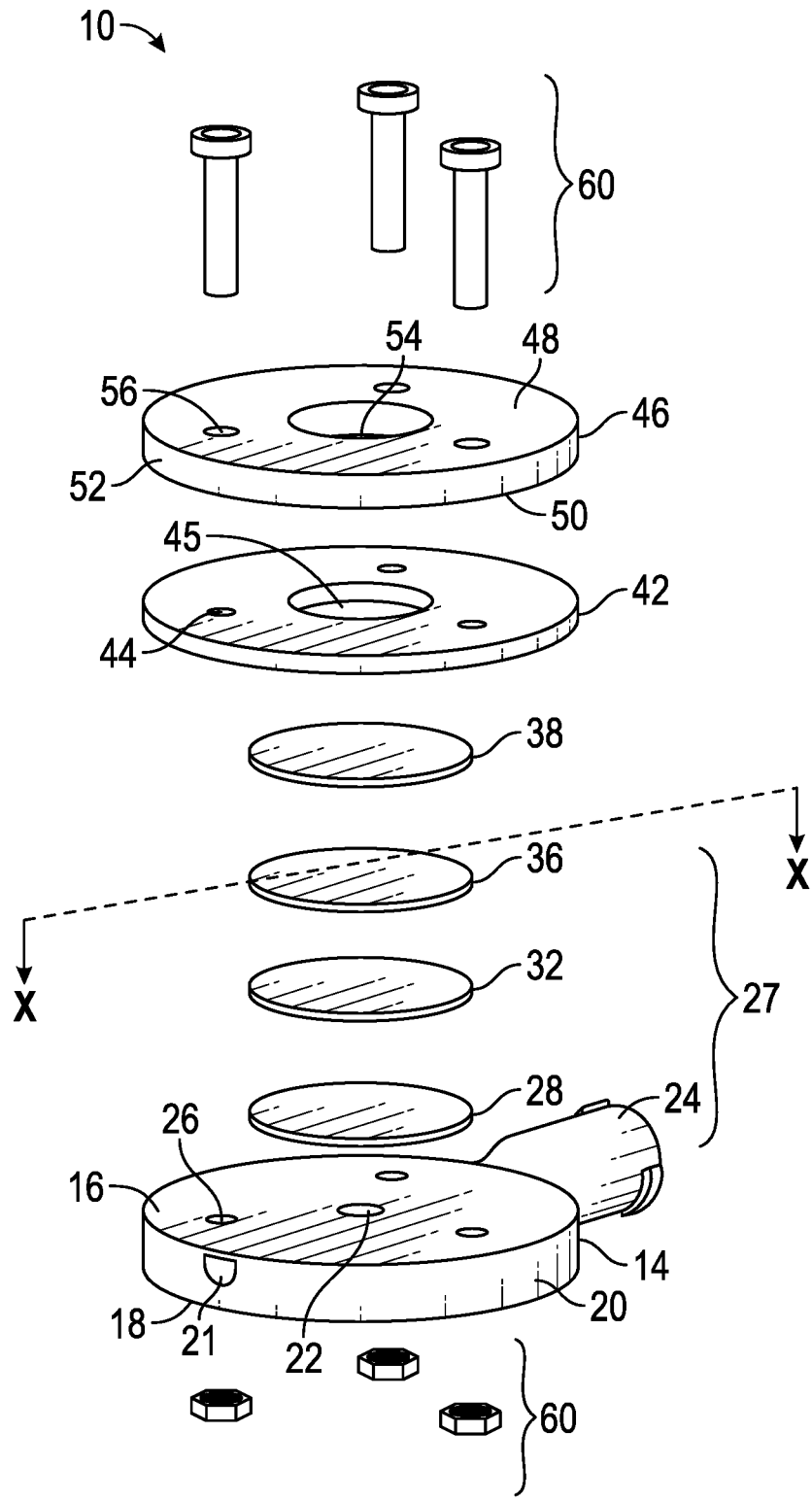
FIG. 1 is a perspective, exploded view of a non-limiting embodiment of a blood testing device constructed in accordance with the presently disclosed and/or claimed inventive concept(s).

The following detailed description refers to the accompanying drawings. The same reference numbers in different drawings may identify the same or similar elements.

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art.

All patents, published patent applications, and non-patent publications mentioned in the specification are indicative of the level of skill of those skilled in the art to which this presently disclosed and claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the devices, kits, and/or methods disclosed and claimed herein can be made and executed without undue experimentation in light of the present disclosure. While the compositions and methods of this presently disclosed and claimed inventive concept(s) have been described in terms of preferred embodiments, it will be apparent to those of skill in the art that variations may be applied to the compositions and/or methods and in the steps or in the sequence of steps of the method described herein without departing from the concept, spirit and scope of the presently disclosed and claimed inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The singular forms "a," "an," and "the" include plural referents unless the context clearly indicates otherwise. Thus, for example, reference to "a compound" may refer to 1 or more, 2 or more, 3 or more, 4 or more or greater numbers of compounds. The term "plurality" refers to "two or more." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by ±20% or ±10%, or ±5%, or ±1%, or 0.1% from the specified value, as such variations are appropriate to perform the disclosed methods and as understood by persons having ordinary skill in the art. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used in this specification and claim(s), the terms "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein, the phrase "associated with" includes both direct association of two moieties to one another as well as indirect association of two moieties to one another. Non-limiting examples of associations include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety.

The term "liquid test sample" as used herein will be understood to include any type of biological fluid sample that may be utilized in accordance with the presently disclosed and claimed inventive concept(s). Examples of biological samples that may be utilized include, but are not limited to, whole blood or any portion thereof (i.e., plasma or serum), saliva, sputum, cerebrospinal fluid (CSF), intestinal fluid, intraperotineal fluid, cystic fluid, sweat, interstitial fluid, tears, mucus, urine, bladder wash, semen, combinations, and the like. The volume of the sample utilized in accordance with the presently disclosed and claimed inventive concept(s) is from about 0.1 to about 100 microliters. As used herein, the term "volume" as it relates to the liquid test sample utilized in accordance with the presently disclosed and claimed inventive concept(s) means from about 0.1 microliter to about 100 microliters, or from about 1 microliter to about 75 microliters, or from about 2 microliters to about 60 microliters, or less than or equal to about 50 microliters, or less than or equal to about 40 microliters. In one non-limiting embodiment of the presently disclosed and/or claimed inventive concept(s), the liquid test sample is a patient's whole blood sample comprising and/or consisting of about 10 microliters to about 30 microliters in volume.

The term "patient" includes human and veterinary subjects. In certain embodiments, a patient is a mammal. In certain other embodiments, the patient is a human. "Mammal" for purposes of treatment refers to any animal classified as a mammal, including human, domestic and farm animals, nonhuman primates, and zoo, sports, or pet animals, such as dogs, horses, cats, cows, etc.

The term "plasma" refers to the liquid component of blood that is responsible for holding the blood cells in a whole blood sample in suspension that carries cells and proteins throughout the body. In one non-limiting embodiment, plasma may comprise and/or consist of dissolved proteins and/or analyte(s), such as, by way of example only, serum albumins, globulins, and fibrinogen, glucose, clotting factors, electrolytes, such as, by way of example only, sodium, calcium, magnesium, potassium, bicarbonate, chloride ions, hormones, carbon dioxide, and oxygen.

Turning now to particular embodiments, the presently disclosed and claimed inventive concept(s) relate to a device(s), kit(s), and method(s) for injecting a patient's liquid test sample into a reaction vessel. More specifically, the presently disclosed and claimed inventive concept(s) relate to an improved liquid test sample injection device that comprises a plug that forms an airtight seal that facilitates the active injection of a liquid test sample into a reaction vessel, and kits and methods of use related thereto.

It is contemplated that virtually any reagent used in the fields of biological, chemical, or biochemical analyses and assays could be used in the devices, kits, and methods of the presently claimed and disclosed inventive concept(s). It is contemplated that these reagents may undergo physical and/or chemical changes when bound to an analyte of interest whereby the intensity, nature, frequency, or type of signal generated by the reagent-analyte complex is directly proportional or inversely proportional to the concentration of the analyte existing within the fluid sample. These reagents may contain indicator dyes, metal, enzymes, polymers, antibodies, and electrochemically reactive ingredients and/or chemicals that, when reacting with an analyte(s) of interest, may exhibit change in color.

Assays, including, but not limited to, immunoassays, nucleic acid capture assays, lipid-based assays, and serology-based assays, can be developed for a multiplexed panel of proteins, peptides, and nucleic acids which may be contained within a liquid test sample, with such proteins and peptides including, for example but not by way of limitation, albumin, microalbumin, cholesterol, triglycerides, high-density lipoproteins, low-density lipoproteins, hemoglobin, myoglobin, α-1-microglobulin, immunoglobulins, enzymes, proteins, glycoproteins, protease inhibitors, drugs, cytokines, creatinine, and glucose. The device(s), kit(s), and method(s) disclosed and/or claimed herein may be used for the analysis of any liquid test sample, including, without limitation, whole blood, plasma, serum, or urine. In accordance with one aspect, there are provided devices, systems, and processes for determining a presence of hemolysis in a sample suspected of having hemolysis (i.e., broken cell red blood cell fragment(s), hemoglobin, etc.).

In certain embodiments of the presently disclosed and/or claimed inventive concept(s), the sample is a whole blood sample which includes a quantity of whole blood cells, including red blood cells, white blood cells, and platelets. Within the sample, the extent of hemolysis may correlate to an amount of hemoglobin therein. As used herein, it is understood that the term "hemoglobin" refers to any and all hemoglobin molecules obtained either from drawn blood, such hemoglobin molecules being in their oxygenated, deoxygenated, dimeric, tetrameric, or various polymerized forms. Hemoglobin is commonly known as the oxygen-carrying pigment and predominant protein of red blood cells. Hemoglobin is composed of four protein chains, two alpha chains and two beta chains, each with a ring-like heme group containing an iron atom. Oxygen binds reversibly to these iron atoms. In its oxygenated state, hemoglobin may be referred to as oxyhemoglobin and is characterized by a bright red color. In the reduced state, hemoglobin may be referred to as deoxyhemoglobin and is characterized by a purple-blue color.

In accordance with another aspect of the presently disclosed and/or claimed inventive concept(s), there are provided devices, systems, and processes for a blood collection assembly having a hemolysis indicating feature.

In accordance with another aspect of the presently disclosed and/or claimed inventive concept(s), there are provided blood testing devices, systems, accessories and processes having a plasma separating feature.

In accordance with another aspect of the presently disclosed and/or claimed inventive concept(s), there are provided blood testing devices, systems, accessories, and processes having a hemolysis indicating feature.

Referring now to the Figures and in particular to FIG. 1, shown therein is a perspective, exploded view of a non-limiting embodiment of a blood testing device 10 constructed in accordance with the presently disclosed and/or claimed inventive concept(s). In this non-limiting embodiment, the blood testing device 10 comprises and/or consists of a base portion 14, a filter assembly 27, a filter assembly cap 38, at least one seal 42 having at least one viewing window 45 disposed therethrough, a top portion 46 having at least one viewing window 54 disposed therethrough, and at least one fastener assembly 60 that secures the various components to one another to form the blood testing device 10.

In one non-limiting embodiment, the base portion 14 comprises and/or consists of a top surface 16, a bottom surface 18, at least one outer side wall 20, at least one liquid sample flow-through port 22 disposed within the top surface 16, a receptacle connector 24, and at least one fastener channel 26. In addition, as discussed in greater detail with respect to FIG. 2, the base portion 14 further comprises an internal cavity 66 that receives the patient's liquid test sample from a receptacle 70 (as shown in FIG. 3).

While shown in FIG. 1 as being substantially circular in shape, a person having ordinary skill in the art should readily appreciate that the base portion 14 can be any shape capable of accomplishing the presently disclosed and/or claimed inventive concept(s), including, without limitation, circular, ovular, triangular, square, rectangular, pentagonal, hexagonal, heptagonal, octagonal, nonagonal, decagonal, hendecagonal, dodecagonal, or a polygon with any number of sides capable of accomplishing the presently disclosed and/or claimed inventive concept(s). In addition, while shown in FIG. 1 as comprising a single liquid sample flow-through port 22 that allows a patient's liquid test sample, such as a blood sample, to flow from the base portion 14 to the first filter 28 (shown in greater detail in FIG. 2), a person having ordinary skill in the art should readily understand that the top surface 16 of the base portion 14 may comprise and/or consist of any number of liquid sample flow-through ports 22 capable of accomplishing the presently disclosed and/or claimed inventive concept(s), including, without limitation, 1, 2, 3, 4, 5, 6, 7, 8, 9, or greater than or equal to 10 liquid sample flow-through ports 22. In addition, while shown in FIG. 1 as comprising a circular liquid sample flow-through port 22, it should be readily understand that the liquid sample flow-through port 22 is not so limited in structure and may comprise one or more trenches, indentations, channels, and/or any other structure capable of accomplishing the presently disclosed and/or claimed inventive concept(s). It should also be understood that while FIG. 1 shows the base portion 14, the at least one seal 42, and the top portion 46 comprising and/or consisting of three fastener channels 26, 44, and 56 respectively, the base portion 14, the at least one seal 42, and the top portion 46 may comprise any number of fastener channels capable of accomplishing the presently disclosed and/or claimed inventive concept(s), including, without limitation, 1, 2, 3, 4, 5, 6, 7, 8, 9, or greater than or equal to 10 fastener channels. The blood testing device 10 need not have any fastener channels, as the various components forming the blood testing device 10 may be joined or mated together via any method commonly known in the art, including, without limitation, via use of adhesive(s) commonly known in the art.

As shown in FIG. 1, in one non-limiting embodiment the at least one outer side wall 20 may comprise and/or consist of a port 21. In one non-limiting embodiment, the port 21 serves to dissipate any displaced air created when utilizing the receptacle 70 (as shown in greater detail in FIG. 3) to introduce a patient's liquid test sample into the filter assembly 27. In another non-limiting embodiment, the port 21 may be replaced with a connection mechanism (not shown) that secures the blood test device 10 (or blood testing assembly 100) to an instrument, for instance, by way of example, a blood gas analyzer. In one non-limiting embodiment, the connection mechanism may be, by way of example only, a luer lock or male and female mating connection or any other structure capable of accomplishing the presently disclosed and/or claimed inventive concept(s). Accordingly, a user can check for the presence of hemolysis in a patient's plasma sample either before, during, or after the sample is transported via the connection mechanism to the instrument.

The base portion 14 may be formed from any suitable liquid impermeable material that is also inert to at least hemoglobin. For example, without limitation, the base portion 14 may be formed from a material comprising polystyrene, polyethylene, polycarbonate, polypropylene, fluoropolymer, polyester, glass, metals, ceramics, suitable composite materials, and combinations thereof as would be appreciated by those skilled in art. Further, the base portion 14 may be constructed of a material that is opaque to light in the visible part of the electromagnetic spectrum.

Figure 2:
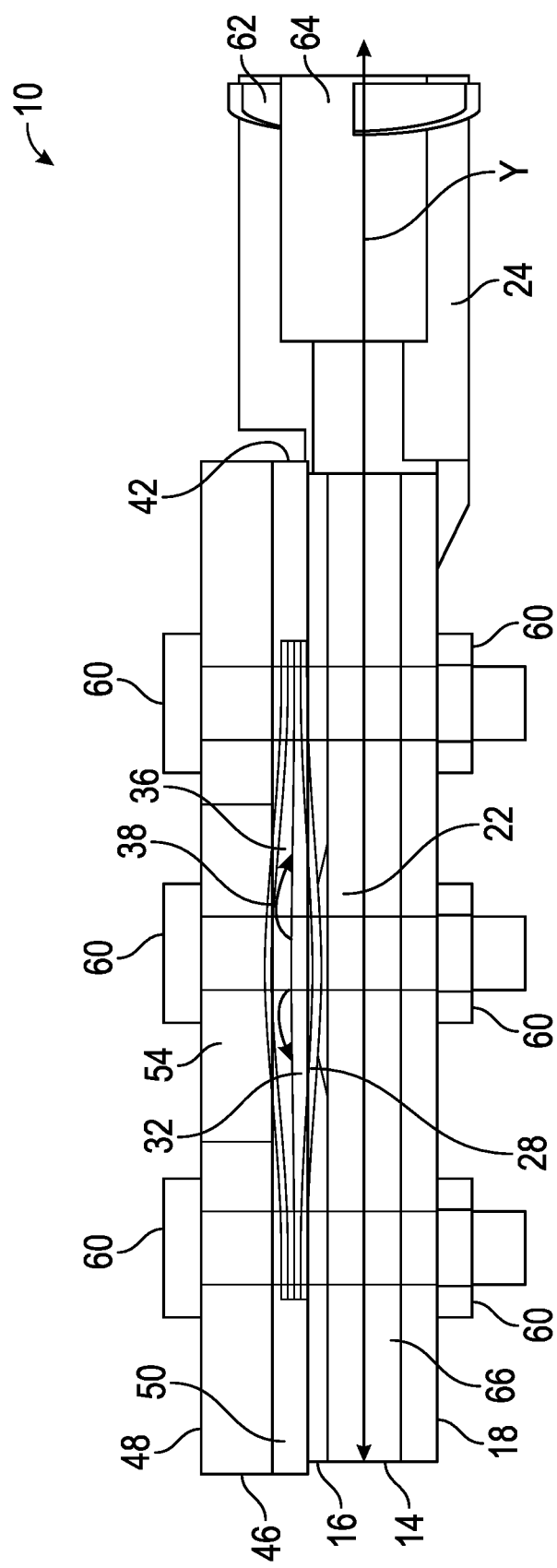
FIG. 2 is a cross-sectional view of the blood testing device of FIG. 1 as viewed along cross-sectional arrow x in which a patient's blood sample is flowing through an internal cavity of a base portion of the blood testing device.
Figure 3:
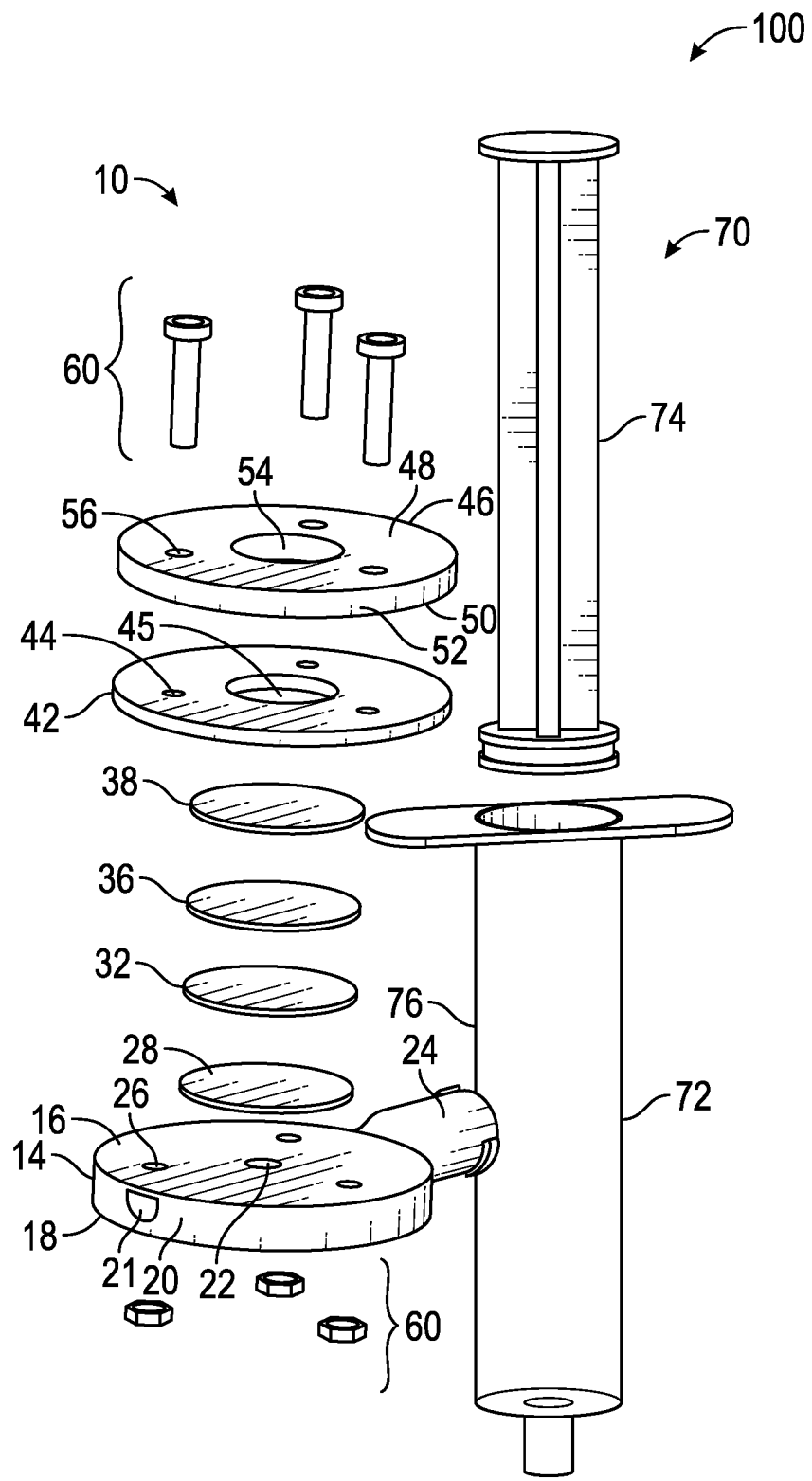
FIG. 3 is a perspective, exploded view of the blood testing device of FIG. 1 attached to a receptacle to a form a blood testing assembly in accordance with the presently disclosed and/or claimed inventive concept(s).

In one non-limiting embodiment, the at least one liquid sample flow-through port 22 is disposed within the top surface 16 of the base portion 14 and in fluid communication with at least a portion of an internal cavity 66 (as shown in FIG. 2). The internal cavity 66 receives a patient's liquid test sample from a receptacle 70 (as shown in FIG. 3) via the receptacle connector 24, the receptacle connector 24 connecting the blood testing device 10 to the receptacle 70.

In one non-limiting embodiment, and as shown in FIG. 1, the filter assembly 27 comprises and/or consists of a first filter 28, a second filter 32, and an optional third filter 36. While shown in FIG. 1 as comprising and/or consisting of three separate filters, a person having ordinary skill in the art should readily appreciate that the filter assembly 27 may comprise any number of filters capable of accomplishing the presently disclosed and/or claimed inventive concept(s), including, without limitation, 1, 2, 3, 4, 5, 6, 7, 8, 9, or greater than or equal to 10 filters. As shown in FIG. 1, the first filter 28, the second filter 32, and the third filter 36 may be aligned and stacked one on top of the other. The first filter 28, second filter 32, and third filter 36 may be the same size and shape, e.g., in the embodiment shown in FIG. 1 the first filter 28, second filter 32, and third filter 36 are circular in shape. However, it should be readily understood to a person having ordinary skill in the art that the first filter 28, second filter 32, and third filter 36 may be different sizes and/or shapes. The filter assembly 27 is configured such that the flow of the patient's liquid test sample in the internal cavity 66 of the base portion 14 is tangent to the filter assembly 27 (i.e., the flow of the patient's liquid test sample is parallel to the filter assembly). Via, for instance, capillary action, the whole blood and plasma flow parallel/tangent to the filter assembly 27 and travel perpendicularly through the various filters of the filter assembly 27, which reduces both the time to results and sample waste, as well as preventing impeded work flow resulting from, for instance, the clogging of the filter assembly 27 by the patient's liquid test sample (e.g., a patient's whole blood sample).

In one non-limiting embodiment, the first filter 28 of the filter assembly 27 is disposed on the top surface 16 of the base portion 14 over at least a portion of the liquid sample flow-through port 22. Accordingly, when a patient's liquid test sample is present within the internal cavity 66 of the base portion 14, the liquid test sample is pushed through the liquid sample flow-through port 22 and is pulled into the first filter 28, for instance, via capillary action, and any air present therein is displaced internally, for instance, either to the edges of the blood testing device 10 or through the various filters comprising the filter assembly 27. The first filter 28 may be designed to separate various blood cells comprising a patient's whole blood sample from the plasma, and then to pass the plasma to the second filter 32. For example, in the embodiment shown in FIG. 1, the first filter 28 may isolate plasma and hemolysis products, e.g., hemoglobin, from whole blood cells in a patient's whole blood sample. In an embodiment, the first filter 28 comprises a plasma separation membrane as is commercially available in the art. In certain embodiments, the plasma separation membrane comprises an asymmetric material, which is able to retain a plurality of whole blood cells thereon while allowing plasma and small molecules/complexes to travel there through. A number of different plasma separation membranes are commercially available and may be suitable for use in the blood testing device 10. For example, the plasma separation membrane may comprise an asymmetric polysulfone material as is commercially available from Pall Corporation (currently sold under the trademark Vivid™). Alternatively, the first filter 28 may comprise any other suitable material or device that can provide a sample comprising plasma and components from hemolysis (if present) therein.

Once the plasma is separated from the patient's whole blood sample by the first filter 28 of the filter assembly 27, the separated plasma is provided to the second filter 32. The second filter 32 is provided with a predetermined color and forms a background and may comprise and/or consist of at least one reagent that reacts with hemoglobin if present in the separated plasma; however, it should be readily understood that the second filter 32 need not comprise and/or consist of at least one reagent in order to accomplish the presently disclosed and/or claimed inventive concept(s). The plasma is pulled into and saturates the second filter 32, for instance, via capillary action. If present on the second filter 32, the at least one reagent (not shown) reacts with the plasma and may change color to indicate a state of hemolysis, or an unacceptable level of hemolysis. The second filter 32 provides a consistent color background, and therefore assists with the colorimetric comparison of the color of the at least one reagent which, in one non-limiting embodiment, is disposed on the third filter 36. In one non-limiting embodiment, the second filter 32 is black filter paper, although it should be understood that other colors could be used.

A non-exhaustive list of reagents that may utilized to show a color change in the presence of various analytes in accordance with the presently disclosed and/or claimed inventive concept(s) are shown below in Table 1.

TABLE 1

| Assay Purpose (and simplified formula) | Approximate Time to Results |
|---|---|
| Membrane (color change) | 30 seconds |
| Blood: This test is based on the peroxidase-like activity of hemoglobin which catalyzes the reaction of diisopropylbenzene dihydroperoxide (w/w 6.8%) and 3,3',5,5'tetramethylbenzidine (w/w 4%). The resulting color ranges from orange through green. Very high levels may continue color development to blue | <60 seconds |
| Protein-Low (Albumin): This test is based on dye binding using a high affinity sulfonephthalein dye. At a constant pH, the development of any color ranging from pale green to aqua blue. Ingredients: 1.9% w/w bis (3',3"-diiodo-4',4"-dihydroxy-5',5"-dinitrophenyl)-3,4,5,6-tetrabromosulfonephthalein | <50 seconds |
| Protein-High: This test is based on the protein-error-of-indicators principle. At a constant pH, the development of any green color is due to the presence of protein. Controls range from yellow, low-green, green, and green-blue. Ingredients: 0.3% w/w tetrabromphenol blue | <50 seconds |

As discussed elsewhere herein, the filter assembly 27 may comprise and/or consist of a third filter 36 on which may be incorporated at least one reagent that enhances the detection and visualization of hemoglobin when hemolysis is low in the plasma sample. Such reagents are detailed in Table 1 above. The separated plasma sample passes from the second filter 32 to the third filter 36 via, for instance, capillary action. In one non-limiting embodiment, the third filter 36 is white filter paper, although it should be understood that other colors could be used. In another non-limiting embodiment, there is no reagent disposed on the third filter 36 of the filter assembly 27; rather, if hemoglobin is present within the separated plasma sample, the hemoglobin may change the color of the third filter 36 (i.e., the white filter paper) upon the third filter 36 coming into contact with the separated plasma sample containing hemoglobin as a result of hemolysis. The third filter 36 is provided with a predetermined color and forms a background and may comprise and/or consist of at least one reagent that reacts with hemoglobin if present in the separated plasma; however, it should be readily understood that the third filter 36 need not comprise and/or consist of at least one reagent in order to accomplish the presently disclosed and/or claimed inventive concept(s).

The blood testing device 10 further comprises and/or consists of a filter assembly cap 38 that is disposed over either a portion of or the entirety of the filter assembly 27. In one non-limiting embodiment, and as shown in FIG. 1, the filter assembly cap 38 is substantially the same size and shape (i.e., circular) as the filters comprising the filter assembly 27; although it should be understood that the filter assembly cap 38 may be the same or different in both size(s) and shape(s) of the filters comprising the filter assembly 27. In one non-limiting embodiment, the filter assembly cap is constructed of a substantially transparent material(s) so as to allow for the viewing of the color change(s) associated with the second filter 32 and/or the third filter 36 of the filter assembly 27 resulting from the reaction of the analyte(s) of interest (i.e., hemoglobin) with the at least one reagent(s) disposed on the second filter 32 and/or third filter 36. Suitable materials for constructing the filter assembly cap 38 include, but are not limited to, polystyrene, polyethylene, polycarbonate, polypropylene, fluoropolymer, polyester, glass, suitable composite materials, and combinations thereof as would be appreciated by those skilled in art. The filter assembly cap 38 also acts to seal the filter assembly 38 which aids in the mitigation of evaporation of the plasma sample from the filter assembly 27. In addition, the sealing of the filter assembly 27 by the filter assembly cap 38 further acts to mitigate or eliminate a user from being exposed to potentially biohazardous materials.

In one non-limiting embodiment, the blood testing device 10 further comprises and/or consists of at least one seal 42 having at least one viewing window 45 disposed therethrough. As shown in FIG. 1, in one non-limiting embodiment the at least one seal 42 is substantially the same size and shape as the top surface 16 of the base portion 14 (i.e., circular); however, it should be understood that the at least one seal 42 may be the same or different in both size and shape of the top surface 16 or the base portion 14. In one non-limiting embodiment, the at least one seal 42 is disposed over the entirety of the top surface 16 of the base portion 14, the filter assembly 27, and the filter assembly cap 38 thereby facilitating the sealing of the filter assembly 27 and filter assembly cap 38 between the top surface 16 of the base portion 14 and a bottom surface 50 of the top portion 46. The at least one seal 42 further comprises a plurality of fastener channels 44 which engage with the fastener assembly 60 to thereby secure and form the blood testing device 10.

In one non-limiting embodiment, the at least one seal is a gasket formed from materials commonly known in the art.

The at least one viewing window 45 disposed through the at least one seal 42 is oriented such that the at least one viewing window 45 is substantially disposed over the filter assembly cap 38 such that a user is able to view any color changes associated with the reaction(s) between the at least one reagent(s) present on the second filter 32 and the third filter 38 and the patient's plasma sample that are indicative of the presence of an analyte(s) of interest—such as, by way of example, the presence of hemoglobin in the plasma sample resulting from hemolysis.

The blood testing device 10 further comprises and/or consists of a top portion 46 that comprises a top surface 48, a bottom surface 50, at least one outer side wall 52, at least one viewing window 54 disposed therethrough extending between the top surface 48 and the bottom surface 50, and at least one fastener channel 56.

While shown in FIG. 1 as being substantially circular in shape, a person having ordinary skill in the art should readily appreciate that the top portion 46 can be any shape capable of accomplishing the presently disclosed and/or claimed inventive concept(s), including, without limitation, circular, ovular, triangular, square, rectangular, pentagonal, hexagonal, heptagonal, octagonal, nonagonal, decagonal, hendecagonal, dodecagonal, or a polygon with any number of sides capable of accomplishing the presently disclosed and/or claimed inventive concept(s). The top portion 46 may be formed from any suitable liquid impermeable material that is also inert to at least hemoglobin. For example, without limitation, the top portion 46 may be formed from a material comprising polystyrene, polyethylene, polycarbonate, polypropylene, fluoropolymer, polyester, glass, metals, ceramics, suitable composite materials, and combinations thereof as would be appreciated by those skilled in art. Further, the top portion 46 may be constructed of a material that is opaque to light in the visible part of the electromagnetic spectrum.

The at least one viewing window 54 of the top portion 46 is oriented such that at least one viewing window 54 is substantially aligned with and disposed over the at least one viewing window 45 of the at least one seal 42. Accordingly, by looking through the at least one viewing window 54 of the top portion 46, a user can view any color changes associated with the second filter 32 and/or the third filter 36 resulting from a reaction(s) between the at least one reagent(s) disposed on the second filter 32 and/or third filter 36 and an analyte(s) of interest present within the patient's liquid test sample—such as, by way of example, the hemoglobin present within a patient's separated plasma sample.

As shown in FIG. 1, the top portion 46 further comprises a plurality of fastener channels 56 disposed through the top portion 46. In one non-limiting embodiment, the plurality of fastener channels 56 of the top portion 46 are configured so as to be aligned with the fastener channels 44 of the at least one seal 42, and the fastener channels 26 of the base portion 14. Accordingly, when engaged, the fastener assembly 60 fits through the fastener channels 56 of the top portion 46, the fastener channels 44 of the at least one seal 42, and the fastener channels 26 of the base portion 14 thereby securing and sealing the filter assembly 27, the filter assembly cap 38, and the at least one seal 42 between the base portion 14 and the top portion 46 to form the blood testing device 10. In one non-limiting embodiment, the fastener assembly 60 comprises and/or consists of a plurality of nuts and bolts, such as, by way of example three 2M bolts and three 2M nuts. In another non-limiting embodiment, the base portion 14, at least one seal 42, and the top portion 46 do not comprise any fastener channels and the blood testing device 10 is formed by adhering the various components to one another via utilizing any adhesive commonly known in the art. The sealing and securement of the blood testing device 10 further prevents or reduces accidental biohazard exposure resulting from the spillage or leaking of the patient's liquid test sample from the sealed blood testing device 10.

Referring now to FIG. 2, shown therein is a cross-sectional view of the blood testing device 10 of FIG. 1 as viewed along cross-sectional arrow x in which a patient's blood sample is flowing through the internal cavity 66 of the base portion 14 of the blood testing device 10.

As shown in FIG. 2, in one non-limiting embodiment, the receptacle connector 24 of the base portion 14 comprises a locking mechanism 62 that secures the blood testing device 10 to a port 76 (shown in FIG. 3) of the receptacle 70 and an opening 64 for receiving the patient's liquid test sample from the port 76 of the receptacle 70 into the internal cavity 66 of the base portion 14 of the blood testing device 10. While shown in FIG. 2 as comprising a luer lock, a person having ordinary skill in the art should readily appreciate that the locking mechanism 62 may secure the blood testing device 10 to the receptacle 70 via any locking mechanism commonly known in the art, including, without limitation, via any male and female mating connection or any other structure capable of accomplishing the presently disclosed and/or claimed inventive concept(s).

Once the blood testing device 10 is secured to the receptacle 70, the patient's liquid test sample (i.e., whole blood sample) enters through opening 64 into the internal cavity 66 of the base portion 14 (for instance, along the path of the bidirectional arrow Y). As shown in FIG. 2, the flow of the patient's liquid test sample is tangent to the filter assembly 27. Once in the internal cavity 66, the patient's liquid test sample flows within the internal cavity 66 (some of which reenters the receptacle via the port 76), while at least a portion of the patient's liquid test sample passes through the at least one sample flow-through port 22 and is pulled into the first filter 28. When the patient's liquid test sample is a whole blood sample, the first filter 28 separates the plasma from the whole blood sample and the separated plasma then passes through, for instance, via capillary action, to the second filter 32. The second filter comprises at least one reagent for detecting an analyte(s) of interest present within the plasma sample, for instance, by way of example, hemoglobin present in the plasma sample as a result of hemolysis. If the analyte of interest is present, the reaction between the at least one reagent and the analyte of interest may result in a color change of the second filter which a user can compare to a known concentration associated with the color change so as to determine the concentration of the analyte of interest (i.e., hemoglobin) present within the patient's liquid test sample (i.e., plasma). If present, the patient's liquid test sample then passes through, for instance, via capillary action, to the third filter 36 which may also comprise at least one reagent that reacts with the patient's liquid test sample (i.e., plasma) if an analyte of interest (i.e., hemoglobin) is present therein resulting in a color change to the third filter 36. Likewise, a user can compare the color change of the third filter 36 to a known concentration associated with the color change/chart so as to determine the concentration of the analyte of interest (i.e., hemoglobin) present within the patient's liquid test sample (i.e., plasma).

As a result of the tangent flow of the patient's liquid test sample within the inner cavity 66 of the base portion 14, the distance that the patient's liquid test sample has to travel vertically through the filter assembly 27 is reduced resulting in a reduction in the time to results. In addition, the tangent flow results in a reduction in the amount of patient's liquid test sample needed to conduct a various test and/or assay. Likewise, sample waste is reduced as is the clogging of the filters comprising the filter assembly 27 thereby preventing impeded workflow.

Referring now to FIG. 3, shown therein is a perspective, exploded view of the blood testing device 10 of FIG. 1 attached to a receptacle 70 to a form a blood testing assembly 100 in accordance with the presently disclosed and/or claimed inventive concept(s).

The functioning and construction of the blood testing device 10 of the blood testing assembly 100 is the identical to the description of the blood testing device 10 described with respect to FIGS. 1 and 2. While the receptacle 70 is shown in FIG. 3 as comprising syringe 72, a plunger 74, and a port 76, a person having ordinary skill in the art should readily appreciate that the receptacle 70 may be any structure capable of accomplishing the presently disclosed and/or claimed inventive concept(s), including, without limitation, a vacutainer having a port to secure the base portion 14 to the receptacle 70.

In operation of the blood testing assembly 100, a sample of blood to be tested is placed within the receptacle 70. The receptacle connector 24 of the base portion 14 of the blood testing device 10 may be connected to the port 76 of the receptacle 70, and an amount of blood is transferred through the port 76 and through the opening 64 of the receptacle connector 24 into the interior cavity 66 of the base portion 14 of the blood testing device 10. As the blood is transferred into the interior cavity 66, air within the interior cavity 66 is directed to the edges of the internal cavity 66. As the blood enters the interior cavity 66, the blood is diffused through the at least one sample flow-through port 22 disposed in the top surface 16 of the base portion 14 and is applied to the first filter 28. The first filter 28 separates the blood cells and platelets from the plasma, and passes the plasma to the second filter 32. The plasma saturates the second filter 32, and, if an analyte(s) of interest in present in the plasma sample, the second filter 32 undergoes a color change due to the reaction between the at least one reagent disposed on the second filter 32 and the analyte(s) of interest (i.e., hemoglobin), the color change being directly related to the concentration of the analyte of interest present in the separated plasma sample. If present, the separated plasma sample then passes from the second filter 32 to the third filter 36. Upon substantially saturating the third filter 36, the third filter 36 may similarly undergo a color change as a result of a reaction between the at least one reagent disposed on the third filter 36 and the analyte(s) of interest (i.e., hemoglobin), the color change being directly related to the concentration of the analyte of interest present in the separated plasma sample. The color changes of the second filter 32 and, if present, the third filter 36 may be viewed by a user through the at least one viewing window of 45 of the seal and the at least one viewing window 56 of the top portion 46. The user can then make a determination of whether the blood has hemolysis by comparing the color of the second filter 32 and, if present, the third filter 36 to known colors indicative of hemolysis and the presence and/or concentration of hemoglobin in a plasma sample (for instance, via a known color chart or calibration curve). Thereafter, the blood testing device 10 may be removed from the receptacle 70 and discarded. When the blood sample does not have an unacceptable level of hemolysis, the blood sample can be tested using conventional techniques, such as providing the blood sample into a cartridge of a blood gas analyzer.

Non-Limiting Examples of the Inventive Concept(s)

A blood testing assembly, comprising: a receptacle containing blood, and having a port configured to transfer the blood out of the receptacle; a blood testing device, comprising: a base portion having a top surface, bottom surface, and at least one outer side wall, the base portion comprising a receptacle connector that connects the base portion to the port of the receptacle, the base portion further comprising an internal cavity between the top surface and the bottom surface for receiving the transfer of blood from the receptacle, the base portion comprising at least one liquid sample flow-through port disposed within the top surface of the base portion and in fluid communication with the internal cavity; a filter assembly, the filter assembly being disposed over at least a portion of the at least one sample flow-through port and in fluid communication therewith, wherein the filter assembly is oriented parallel to a flow of blood within the internal cavity; and a top portion having a top surface, a bottom surface, at least one outer wall, the top portion further comprising at least one viewing window disposed therethrough for viewing the filter assembly.

The blood testing assembly, wherein the filter assembly comprises a first filter, a second filter, and a third filter.

The blood testing assembly, wherein the first filter comprises a plasma separation membrane.

The blood testing assembly, wherein the third filter comprises at least one reagent disposed thereon that changes colors in the presence of an analyte of interest.

The blood testing assembly, wherein the analyte of interest is hemoglobin.

The blood testing assembly, wherein the at least one reagent is selected from the group consisting of diisopropylbenzene dihydroperoxide, 3,3',5,5'-tetramethylbenzidine, and combinations thereof.

The blood testing assembly, wherein first filter is disposed over and on at least a portion of the liquid sample flow-through port, the second filter is disposed over and on the first filter, and the third filter is disposed over and on the second filter.

The blood testing assembly, wherein the blood testing device further comprises a filter assembly cap substantially disposed over the filter assembly.

The blood testing assembly, wherein the blood testing device further comprises at least one seal, the at least one seal having a viewing window disposed therein, the least one seal being disposed between the filter assembly cap and the bottom surface of the top portion such that the viewing window of the at least one seal is aligned with the filter assembly cap and the viewing window of the top portion.

The blood testing assembly, wherein the top portion and the base portion are secured to one another by a fastener assembly passing through at least one fastener channel of the top portion and at least one fastener channel of the base portion to thereby secure the top portion and the base portion to one another.

A blood testing device, comprising: a base portion having a top surface, bottom surface, and at least one outer side wall, the base portion comprising a receptacle connector that connects the base portion to the port of the receptacle, the base portion further comprising an internal cavity between the top surface and the bottom surface for receiving the transfer of blood from the receptacle, the base portion comprising at least one liquid sample flow-through port disposed within the top surface of the base portion and in fluid communication with the internal cavity; a filter assembly, the filter assembly being disposed over at least a portion of the at least one sample flow-through port and in fluid communication therewith, wherein the filter assembly is oriented parallel to a flow of blood within the internal cavity; and a top portion having a top surface, a bottom surface, and at least one outer wall, the top portion further comprising at least one viewing window disposed therethrough for viewing the filter assembly.

The blood testing device, wherein the filter assembly comprises a first filter, a second filter, and a third filter.

The blood testing device, wherein the first filter comprises a plasma separation membrane.

The blood testing device, wherein the third filter comprises at least one reagent disposed thereon that changes colors in the presence of an analyte of interest.

The blood testing device, wherein the analyte of interest is hemoglobin.

The blood testing device, wherein the at least one reagent is selected from the group consisting of diisopropylbenzene dihydroperoxide, 3,3',5,5'-tetramethylbenzidine, and combinations thereof.

The blood testing device, wherein first filter is disposed over and on at least a portion of the liquid sample flow-through port, the second filter is disposed over and on the first filter, and the third filter is disposed over and on the second filter.

The blood testing device, wherein the blood testing device further comprises a filter assembly cap substantially disposed over the filter assembly.

The blood testing device, wherein the blood testing device further comprises at least one seal, the at least one seal having a viewing window disposed therein, the least one seal being disposed between the filter assembly cap and the bottom surface of the top portion such that the viewing window of the at least one seal is aligned with the filter assembly cap and the viewing window of the top portion.

A method, comprising: connecting a blood testing device having a plasma separation membrane and at least one filter comprising a reagent to a syringe containing blood having blood cells and plasma; passing a blood sample of the blood from the syringe through a plasma separation membrane within the blood testing device to separate the plasma from the blood cells, wherein the blood sample flows parallel to the plasma separation membrane; saturating the at least one filter with the separated plasma; and calorimetrically analyzing the reagent disposed on the at least one filter to determine a degree of hemolysis within the blood sample.

From the above description, it is clear that the inventive concepts disclosed herein are well adapted to carry out the objects and to attain the advantages mentioned herein as well as those inherent in the inventive concepts disclosed herein. While presently preferred embodiments of the inventive concepts disclosed herein have been described for purposes of this disclosure, it will be understood that numerous changes may be made which will readily suggest themselves to those skilled in the art and which are accomplished within the scope and coverage of the inventive concepts disclosed and claimed herein.

What is claimed is:

1. A blood testing assembly, comprising: a receptacle containing blood, and having a port configured to transfer the blood out of the receptacle; a blood testing device, comprising: a base portion having a top surface, bottom surface, and at least one outer side wall, the base portion comprising a receptacle connector configured to connect the base portion to the port of the receptacle, the base portion further comprising an internal cavity between the top surface and the bottom surface for receiving the transfer of blood from the receptacle, the base portion comprising at least one liquid sample flow-through port disposed within the top surface of the base portion and in fluid communication with the internal cavity; a filter assembly, the filter assembly being disposed over at least a portion of the at least one sample flow-through port and in fluid communication therewith, wherein the filter assembly is positioned parallel to a direction of flow of blood within the internal cavity; and a top portion having a top surface, a bottom surface, at least one outer wall, the top portion further comprising at least one viewing window disposed therethrough for viewing the filter assembly.

2. The blood testing assembly of claim 1, wherein the filter assembly comprises a first filter, a second filter, and a third filter.

3. The blood testing assembly of claim 2, wherein the first filter comprises a plasma separation membrane.

4. The blood testing assembly of claim 2, the third filter comprises at least one reagent disposed thereon that changes colors in the presence of an analyte of interest.

5. The blood testing assembly of claim 4, wherein the analyte of interest is hemoglobin.

6. The blood testing assembly of claim 5, wherein the at least one reagent is selected from the group consisting of diisopropylbenzene dihydroperoxide, 3,3',5,5'-tetramethylbenzidine, and combinations thereof.

7. The blood testing assembly of claim 2, wherein first filter is disposed over and on at least a portion of the liquid sample flow-through port, the second filter is disposed over and on the first filter, and the third filter is disposed over and on the second filter.

8. The blood testing assembly of claim 1, wherein the blood testing device further comprises a filter assembly cap substantially disposed over the filter assembly.

9. The blood testing assembly of claim 8, wherein the blood testing device further comprises at least one seal, the at least one seal having a viewing window disposed therein, the least one seal being disposed between the filter assembly cap and the bottom surface of the top portion such that the viewing window of the at least one seal is aligned with the filter assembly cap and the viewing window of the top portion.

10. The blood testing assembly of claim 1, wherein the top portion and the base portion are secured to one another by a fastener assembly passing through at least one fastener channel of the top portion and at least one fastener channel of the base portion to thereby secure the top portion and the base portion to one another.

11. A blood testing device, comprising: a base portion having a top surface, bottom surface, and at least one outer side wall, the base portion comprising a receptacle connector configured to connect the base portion to a port of a receptacle, the base portion further comprising an internal cavity between the top surface and the bottom surface for receiving the transfer of blood from the receptacle, the base portion comprising at least one liquid sample flow-through port disposed within the top surface of the base portion and in fluid communication with the internal cavity; a filter assembly, the filter assembly being disposed over at least a portion of the at least one sample flow-through port and in fluid communication therewith, wherein the filter assembly is positioned parallel to a direction of flow of blood within the internal cavity; and a top portion having a top surface, a bottom surface, and at least one outer wall, the top portion further comprising at least one viewing window disposed therethrough for viewing the filter assembly.

12. The blood testing device of claim 11, wherein the filter assembly comprises a first filter, a second filter, and a third filter.

13. The blood testing device of claim 12, wherein the first filter comprises a plasma separation membrane.

14. The blood testing device of claim 12, wherein the third filter comprise at least one reagent disposed thereon that changes colors in the presence of an analyte of interest.

15. The blood testing device of claim 14, wherein the analyte of interest is hemoglobin.

16. The blood testing device of claim 15, wherein the at least one reagent is selected from the group consisting of diisopropylbenzene dihydroperoxide, 3,3',5,5'-tetramethylbenzidine, and combinations thereof.

17. The blood testing device of claim 12, wherein first filter is disposed over and on at least a portion of the liquid sample flow-through port, the second filter is disposed over and on the first filter, and the third filter is disposed over and on the second filter.

18. The blood testing device of claim 11, wherein the blood testing device further comprises a filter assembly cap substantially disposed over the filter assembly.

19. The blood testing device of claim 18, wherein the blood testing device further comprises at least one seal, the at least one seal having a viewing window disposed therein, the least one seal being disposed between the filter assembly cap and the bottom surface of the top portion such that the viewing window of the at least one seal is aligned with the filter assembly cap and the viewing window of the top portion.

* * * * *